United States Patent [19]
Hachey et al.

[11] Patent Number: 5,081,869
[45] Date of Patent: Jan. 21, 1992

[54] METHOD AND APPARATUS FOR THE MEASUREMENT OF THE THERMAL CONDUCTIVITY OF GASES

[75] Inventors: Raynald Hachey, Shipshaw; Daniel Lamarre, Duberger; Jacques Marcotte, Jonquiere, all of Canada

[73] Assignee: Alcan International Limited, Montreal, Canada

[21] Appl. No.: 448,548

[22] Filed: Dec. 11, 1989

Related U.S. Application Data

[63] Continuation-in-part of Ser. No. 307,318, Feb. 6, 1989, Pat. No. 4,918,974.

[51] Int. Cl.⁵ .............................................. G01N 25/18
[52] U.S. Cl. .................................. 73/25.03; 73/19.07
[58] Field of Search ................. 73/25.03, 19.07, 23.42; 338/34

[56] References Cited

U.S. PATENT DOCUMENTS

| | | | |
|---|---|---|---|
| 3,864,959 | 2/1975 | MacDonald | 73/25.03 |
| 4,164,862 | 8/1979 | Jackson | 73/25.03 |
| 4,185,491 | 1/1980 | Owen | 73/31.06 |
| 4,461,166 | 7/1984 | Gatten et al. | 73/25.03 |
| 4,470,298 | 9/1984 | Jibelian | 73/23.42 |
| 4,498,330 | 2/1985 | Hosoya | 73/23.21 |
| 4,533,520 | 8/1985 | Bossart et al. | 73/23.21 |
| 4,541,988 | 9/1985 | Tozier et al. | 73/25.03 |
| 4,685,325 | 8/1987 | Warchol | 73/19.07 |
| 4,829,810 | 5/1989 | Anderson et al. | 73/19.07 |

Primary Examiner—Tom Noland
Assistant Examiner—Joseph W. Roskos
Attorney, Agent, or Firm—Cooper & Dunham

[57] ABSTRACT

New methods and apparatus for the measurement of thermal conductivity of gases employ a single katharometer element comprising a thermistor. In one circuit the thermistor is part of a first potential divider whose output voltage is compared to that of a second reference potential divider by applying them to the inputs of a differential amplifier supplying heating current to the element. In another circuit, in which the katharometer element may be other than a thermistor, the element and a resistor are connected in series to a common reference point of the circuit and are supplied with current so that the voltages across them correspond to their respective resistances; the voltage cross the item not connected to the reference point is transferred to another circuit element that is connected to the reference point so that they can be compared directly. If the temperature of the element changes, changing its resistance, the amplifier output changes the amount of power supplied to the katharometer element to restore it to the predetermined temperature. Passage of a gas with a different thermal characteristic over the element changes its temperature, which is corrected by the circuit so that the element operates at a constant temperature.

34 Claims, 8 Drawing Figures

METHOD AND APPARATUS FOR THE MEASUREMENT OF THE THERMAL CONDUCTIVITY OF GASES

CROSS-REFERENCES TO RELATED APPLICATIONS

This application is a continuation-in-part of our prior application Ser. No. 07/307/318, filed Feb. 6, 1989, now U.S. Pat. No. 4,918,974.

FIELD OF THE INVENTION

This invention is concerned with new methods and new apparatus for the measurement of the thermal conductivity of gases. It is concerned particularly but not exclusively with such methods and apparatus for the measurement of the composition of gas mixtures by measurement of their thermal conductivity, as employed in the measurement of the gas content of molten metals.

REVIEW OF THE PRIOR ART

A commercially important application of the measurement of gas thermal conductivity is the determination of the amount of gas, particularly hydrogen, in a body of molten metal, particularly aluminium and its alloys. The presence of more than a predetermined small amount of hydrogen (e.g. 0.1–0.15 ml $H_2$ per 100 g metal) can have deleterious effects on the properties of the metal, and accurate measurement is therefore necessary to ensure that the content is below this value.

In practice a suitable porous probe, such as that disclosed in our U.S. patent application Ser. No. 07/199,673, filed May 27, 1988, the disclosure of which is incorporated herein by this reference, is immersed in the molten metal and a carrier gas such as nitrogen is circulated in a closed loop between the probe and a katharometer. Gases dissolved in the metal are entrained in the carrier gas in proportion to their concentration in the metal, and if the thermal conductivities of the entrained and carrier gases are sufficiently different, then measurement by the katharometer of this parameter for the carrier gas alone, constituting the reference gas, and for the resultant mixture, constituting the test gas, can be used to determine the concentration of the gas dissolved in the metal.

One type of katharometer apparatus commonly employed hitherto uses two cells electrically connected as two opposed arms of a resistance bridge, one of the cells receiving or containing a reference gas and constituting a reference cell, while the other receives a stream of the test gas to be measured and constitutes the measuring cell. Each cell contains a fine heated platinum wire whose resistance depends upon its temperature, the amount by which the wire is cooled upon passage of the gas through the cell depending upon the gas thermal conductivity, which will usually vary with the gas composition because of the different values for the different gases. The resultant change in the resistance of the measuring cell unbalances the bridge, and the value of the resulting unbalance voltage is a function of the thermal conductivity of the test gas.

The manufacture and operation of katharometer apparatus to give consistent results presents a number of difficulties. It is difficult in the first place to produce commercially two katharometer cells with sufficiently similar static and dynamic characteristics to provide a bridge that can be balanced without the need for static and dynamic correcting circuit elements. The two cells should be kept as closely as possible at the same temperature, but this is difficult to achieve when the filament of the measurement cell inherently varies in temperature to provide the necessary unbalance. It is usual therefore to try to maintain the two cells at some standard temperature so as to match their responses as closely as possible. A typical range of hydrogen gas concentration in molten aluminium is 0.1 to 0.3 $mlH_2/100$ g corresponding to 1%–9% by volume in the carrier gas, but it is possible for the percentage to be as high as 25%, and it is not unknown for this type of katharometer to be unable to measure values above 0.4, so that accurate measurement of these higher values becomes impossible.

Attempts, have been made to avoid this problem by providing a katharometer using a single cell. U.S. Pat. No. 4,685,325 discloses such a single cell katharometer in which the cell is supplied with current from a constant current source to heat its filament. A balancing circuit is connected across the cell to balance the current against this constant current source, so that the output voltage is zero when the carrier gas along is passing through the cell, the voltage change developed across the filament being a function of the proportion of hydrogen in the carrier gas.

U.S. Pat. No. 4,829,819 discloses a katharometer employing a single heated filament cell connected in a bridge circuit as one arm thereof and heated by the flow of electric current through it. The filament is maintained by feedback to the bridge circuit at a constant value of resistance and hence at a constant temperature. The bridge and the filament are supplied with a highly stable voltage, and the change in electrical power that must be supplied to the filament to maintain it at the constant resistance value provides a measure of the gas thermal conductivity of the test gas.

DEFINITION OF THE INVENTION

It is the principal object of the present invention to provide new methods for the measurement of gas thermal conductivity.

It is another principal object to provide new apparatus for such measurement employing a single temperature sensitive element.

In accordance with the present invention there is provided a method for the measurement of gas thermal conductivity employing a katharometer comprising a katharometer enclosure enclosing a katharometer element having a temperature resistance characteristic, the method including:

passing a test gas whose thermal conductivity is to be measured into the katharometer enclosure over a thermistor element to thereby change its temperature from a predetermined value and thereby change its resistance from a corresponding value;

employing the change of resistance of the thermistor to change the supply of electrical power to the thermistor to restore its temperature to the predetermined value and its resistance to the corresponding value; and measuring the amount of power supplied to the thermistor with its temperature restored to the predetermined value to determine the test gas thermal conductivity.

Also in accordance with the invention there is provided apparatus for the measurement of gas thermal conductivity comprising:

a katharometer body providing an enclosure in its interior having an inlet thereto and an outlet therefrom;

a thermistor element having a temperature/resistance characteristic mounted within the enclosure;

means for supplying electric power to the thermistor to heat it;

means for supplying a gas whose conductivity is to be measured to the interior of the enclosure to thereby change the temperature of the thermistor from a predetermined value and thereby change its resistance from a corresponding value;

control means responsive to the change of resistance of the thermistor to change the amount of electric power supplied to the element to maintain its temperature at the predetermined value and its resistance at the corresponding value; and means for measuring the amount of power required to maintain the thermistor at its predetermined temperature to provide a measurement representative of the thermal conductivity of the gas.

Further in accordance with the invention there is provided a method for the measurement of gas thermal conductivity employing a katharometer comprising a katharometer enclosure enclosing a katharometer element having a temperature resistance characteristic, the method including:

passing a test gas whose thermal conductivity is to be measured into the katharometer enclosure over the element to thereby change its temperature from a predetermined value and thereby change its resistance from a corresponding value;

employing the change of resistance of the element to change the supply of electrical power by a power supply circuit to the element to restore its temperature to the predetermined value and its resistance to the corresponding value; and measuring the amount of power supplied to the thermistor with its temperature restored to the predetermined value to determine the test gas thermal conductivity;

wherein a resistor is connected in series with the thermistor to a reference point in the circuit;

the resistor and the thermistor are supplied with current from the same source to establish voltages across them corresponding to their respective resistances, one of which voltages is measurable from said reference point;

the voltage across at least the other one of the resistor and thermistor not connected directly to the reference point is transferred to another circuit element connected to the reference point; and the voltages having the reference point in common are compared and the current supplied to the resistor and the thermistor by the circuit is controlled in response to the comparison.

Further in accordance with the invention there is provided apparatus for the measurement of gas thermal conductivity comprising: a katharometer body providing an enclosure in its interior having an inlet thereto and an outlet therefrom;

a katharometer element having a temperature/resistance characteristic mounted within the enclosure;

means for supplying electric power to the element to heat it;

means for supplying a gas whose conductivity is to be measured to the interior of the enclosure to thereby change the temperature of the element from a predetermined value and thereby change its resistance from a corresponding value;

control means responsive to the change of resistance of the element to change the amount of electric power supplied to the element to maintain its temperature at the predetermined value and its resistance at the corresponding value; and means for measuring the amount of power required to maintain the element at its predetermined temperature to provide a measurement representative of the thermal conductivity of the gas;

wherein the control means comprises a resistance connected in series with the element;

means for supplying electrical power to the element and the resistance in series to produce voltages across each of them corresponding to their respective resistances;

means for transferring at least one of the voltages thus produced as a first transfer voltage to a common reference point of the circuit with the other voltage; and means for comparing the two voltages having the common reference point and controlling the supply of electrical power to the element and resistance in series in accordance with the comparison of the two voltages.

DESCRIPTION OF THE DRAWINGS

Particular preferred embodiments of the invention will now be described, by way of example, with reference to the accompanying drawings, wherein.

DESCRIPTION OF THE PREFERRED EMBODIMENTS

Figure 1:
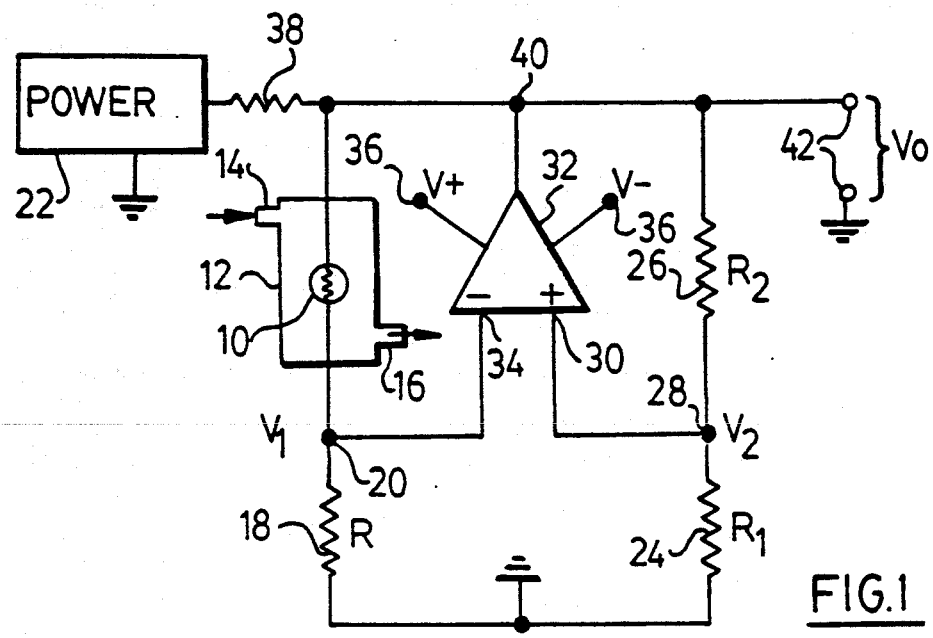
FIG. 1 is a schematic circuit diagram of a first embodiment.

The apparatus of the invention specifically described herein employs a thermistor 10 as a temperature sensitive resistance device whose electrical resistance varies with its absolute temperature, with the absolute value of its resistance being sufficiently constant for a predetermined temperature value. In the embodiments illustrated the thermistor is mounted in the usual relatively heavy metal katharometer enclosure 12 having a gas inlet 14 and a gas outlet 16, so that respective streams of the test and reference gases can be passed through the enclosure interior. In this embodiment the element is connected in series with a fixed resistor 18 of resistance R to provide a first potential divider having a junction 20 at which a voltage $V_1$ will appear, the divider being supplied with electric power from a source 22.

Two series-connected fixed resistors 24 and 26, respectively of resistance $R_1$ and $R_2$, constitute a second reference potential divider, also supplied from the source 22 and have their junction 28 connected to one input terminal 30 of a differential amplifier 32 so as to apply a reference voltage $V_2$ thereto, the junction 20 being connected to the other amplifier input terminal 34. The amplifier is supplied with power from terminals 36 and a start-up load resistor 38 is connected between the source 22 and the circuit to set the start-up voltage (positive or negative) that is applied to the cell.

The thermistor 10 will be heated by the current passing through it and as its temperature increases its resistance decreases, decreasing the value of $V_1$. If the potentials $V_1$ and $V_2$ are not equal the amplifier 32 produces a change in its output voltage proportional to their difference that heats the thermistor 10 further, and thus further decreases its resistance until balance is reached, at which point the element is at a steady temperature and corresponding steady resistance value. In this steady state a constant voltage $V_0$ will be produced at the output terminal 40 of the amplifier and can be measured between the output terminal 42. If a stream of a gas of higher thermal conductivity is now introduced into the katharometer the thermistor 10 cools resulting in an increase in its electrical resistance so that $V_1$ decreases, which results in an increase in the voltage $V_0$ and an increase in the current through the thermistor and resistor 18 to increase the electrical power (energy per second) supplied to the thermistor until its temperature and resistance and restored to the predetermined values. The new value of the voltage $V_0$ is correlated with the gas thermal conductivity of the mixture of gases in the stream by the relation:

$$V_0^2 = \frac{R}{C_r} \cdot \frac{(R_1 + R_2)^2}{R_1 \cdot R_2} \cdot (T_t - T_6) \cdot \left[ K_L + \frac{K_i \cdot K_m}{(K_i \cdot K_m)} \right] \quad (1)$$

where:
R is the resistance of resistor 18;
$R_1$ is the resistance of resistor 26;
$R_2$ is the resistance of resistor 24;
G is a geometrical constant of the katharometer based on the geometry of the katharometer cell and of the thermistor and its disposition in the cell;
$T_t$ is the temperature of the thermistor 10 and is to be as constant as possible;
$T_b$ is the ambient temperature of the katharometer body measured in degrees Kelvin;
$K_L$ is an equivalent gas thermal conductivity corresponding to the heat loss (leakage) by the thermistor electrical leads and is to be maintained as small and constant as possible;
$K_i$ is the equivalent gas thermal conductivity corresponding to the thermal resistivity of the thermistor 10 and is therefore a constant; and
$K_m$ is the thermal conductivity of the test gas to be determined and is therefore variable.

This equation contains a thermal model describing the operation of the katharometer circuit just described and can be regarded as comprising three parts. The left hand part involving resistance values describes the electrical dependence of the configuration of the circuit. The centre part involving temperature values embodies an important consequence of the fact that the value of $T_t$ is constant, which means that either $T_b$ must be known accurately, using an independent measuring instrument such as a thermometer, or the ratio of two measurements taken very close together in time is used, when $T_b$ has not changed substantially if at all and this factor can be eliminated from the final result. The right hand part of the equation describes a specific simplified but sufficiently accurate thermal model of the operation of the katharometer. One of the parameters is the unknown value Km to be measured, and it is necessary to obtain suitable values for $K_i$ and $k_L$; these are obtained from measurements of any three known gases, preferably nitrogen, argon and helium (or hydrogen) made at a given temperature, the values being obtained from the ratio of the resultant Vo values.

Since the left hand part of the relation is dependent upon the specific electrical circuit of the katharometer it can itself be regarded as a circuit constant, when the relation will have the more general form below that is applicable also to other types of katharometer:

$$\text{POWER} = \frac{1}{G} \cdot (T_t - T_6) \cdot \left[ K_L + \frac{K_i \cdot K_m}{(K_i + K_m)} \right] \quad (2)$$

The total electric power that is supplied to the element 10 can be determined by the relation:

$$\text{POWER} = \frac{V_0^2}{R} \cdot \frac{R_1 \cdot R_2}{(R_1 + R_2)^2} \quad (3)$$

Since it is the amount of power (energy per second) that is supplied to the thermistor 10 that maintains its temperature, either the voltage or the current can be measured to obtain a measurement representative of the gas thermal conductivity, since all of the resistances in the circuit are known and are of constant value, the measurement of the voltage usually being preferred.

Figure 2:
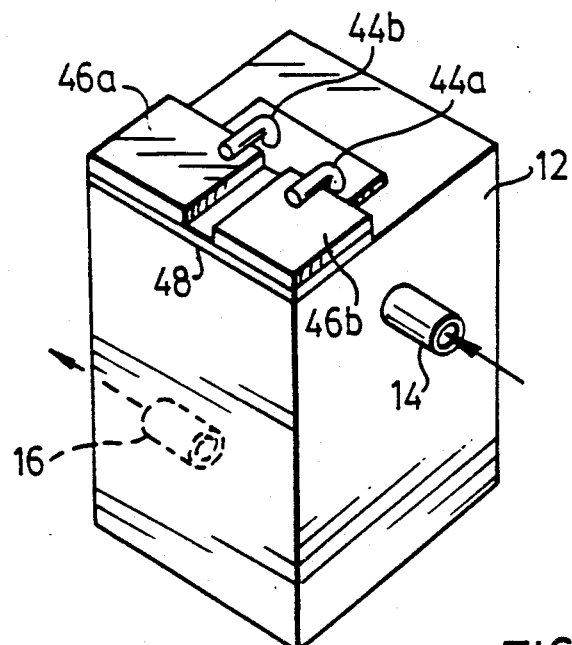
FIG. 2 is a diagrammatic view of a temperature sensitive element illustrating the use of isothermal heat sink plates to stabilize the temperature of its leads.

The value of $K_L$ can be kept at a substantially constant value by an arrangement such as that illustrated by FIG. 2, in which the lead wires 44a and 44b to the thermistor are kept as short as possible and welded independently to respective isothermal heat sinks 46a and 46b, constituted in this embodiment by copper plates, the plates being cemented to a support block 48 attached to the enclosure 12 and electrically insulated from the enclosure and from one another. It will be noted that it is immaterial whether $V_0$ is positive or negative, and this has no effect on the measurement of Km, since the term $V_0^2$ appears in the relation (1). In a specific embodiment the thermistor 10 was obtained from Gow-Mac Corporation, having an internal resistance of 8 Kohm at 25° C. The value of R was 1K and that of $R_1$ and $R_2$ was 10K all three being metal film type of 1% tolerance with thermal coefficient of ±50 ppm per °C. The value of resistor 38 was 22 K. The amplifier was type LT1013AM and the values of V+ and V− were respectively +15 and −15 volts.

In using the katharometer to measure the percentage of hydrogen in molten aluminium it is connected in a closed circuit with a porous probe, such as that described in our above-identified Patent. Pure nitrogen is first injected through the katharometer into the probe immersed in the aluminium and a first reading of $V_0$ is taken. The gas is then circulated continuously between the probe and katharometer in the closed circuit while hydrogen from the aluminium accumulates in the nitrogen carrier gas until equilibrium is reached, based on the respective partial pressures, this usually taking about ten minutes; a second reading of $V_0$ is then taken, from which the gas thermal conductivity is determined. This is also the operating procedure used with prior at apparatus. During this relatively long period the temperature of the block 48 and also of the enclosure 12 can change by several degrees, with the result that the first reading is no longer a valid zero reading.

According in a method of the invention a first reading is taken after the carrier nitrogen has been circulated until the equilibrium with the entrained hydrogen is obtained; immediately after taking this reading pure nitrogen is injected into the circuit to purge the cell of the gas mixture and a second reading is taken about 10-30 seconds, preferably about 15-20 seconds, after the first reading. The katharometer body 12 is a relatively large heat sink and any changes in its temperature therefore take place very slowly, so that the effect of these changes is minimized. The hydrogen concentration is determined by calculation from the two closely-timed thermal conductivity readings that are obtained; since the temperature differences are minimized the precision of measurement is increased.

The new apparatus thus uses a single thermal element and precision can be maintained even with relatively wide changes in the ambient temperature of the katharometer between 10° C. and 60° C. Such a wide temperature variation is encountered in the field environment of an industrial operation, for example in an aluminium melting installation where the apparatus must be used close to the furnace or the metal transfer runner. This precision can be obtained by use of a single measurement provided the temperature of the katharometer body is known to within 0.01° C., or if two closely timed readings are compared as just described above. It will be seen in particular that the control of the temperature of the thermistor 10 is simple in that it is only necessary to control its electrical resistance; the device can be operated at any convenient temperature above the gas temperature within its normal temperature range and it is only necessary for it to be maintained constant at that temperature.

The lower thermal conductivity values can be measured with absolute precision to within ±0.03%. The corresponding precision of percentage of hydrogen in the hydrogen/nitrogen gas mixture is about 1% relative on a 1% hydrogen mixture. The signal level obtainable is dependent on the resistance values of the components, particularly that of the thermistor 10, and is independent of its resistance/temperature characteristic. It is also possible to measure the higher values (up to 100% hydrogen) with adequate dynamic signal range and without saturation of the associated amplifier. With prior art apparatus a substantial inaccuracy was caused by the fact that the measurments were made at temperatures which were not necessarily constant from measurement to measurement, and the thermal conductivities of all gases change with temperature; with the methods and apparatus of the invention the measurements are effectively ratios at the same temperature and these differences therefore disappear to make the measurements virtually temperature insensitive over the operating range.

The desired performance characteristic for industrial test equipment used to determine the hydrogen content of aluminium is the ability to measure, under field conditions, over the ambient temperature range of 10° C.-60° C., such contents to 1% relative to 1% concentration of the hydrogen in the nitrogen carrier gas at 60° C. Such precision has previously been only achievable under laboratory conditions, but has been achieved under field conditions with the methods and apparatus of the invention.

Thermistors which are solid state temperature sensitive devices, usually consisting of a small bead of ceramic material, are unexpectedly particularly advantageously used as the temperature sensitive component of the katharometers. In general their resistance correlates accurately and uniformly with their corresponding operating temperature and they are readily commercially available with a wide range of temperature/resistance characteristics such that it is possible to accomodate the necessary broad operating temperature range of 10° C.-60° C. They are readily available with a temperature/resistance characteristic that is negative over the desired operating range, (i.e. the resistance decreases with increase in temperature), as contrasted with the positive characteristic of the hot filament katharometer elements used hitherto, and this simplifies the design of the accompanying electronic circuit. They are moreover more physically rugged than a heated filament.

Figure 3A:
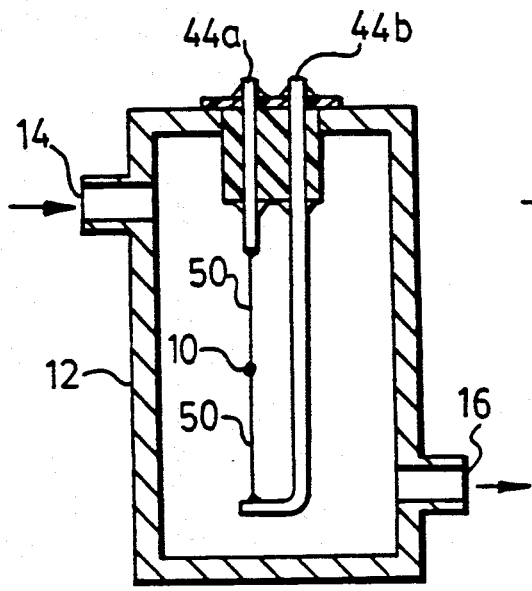
FIGS. 3A and 3B illustrate respectively the manner in which typically a thermistor and a heated filament may be mounted in a katharometer body.
Figure 3B:
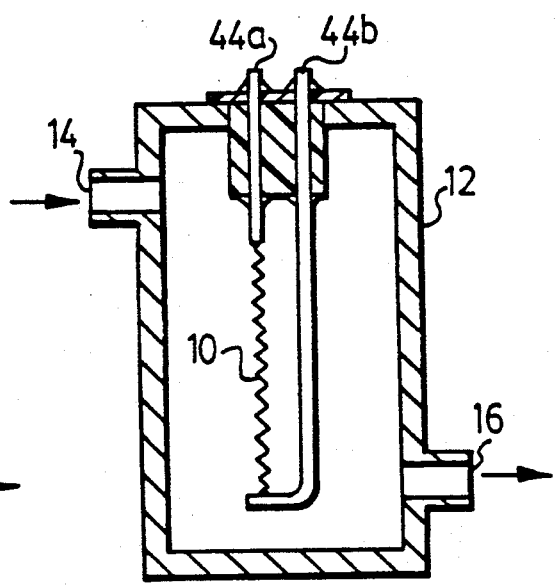

Thermistors of bead form have a specific thermal advantage in a katharometer following from their structure, as is illustrated by FIGS. 3A and 3B, which show respectively a typical mounting for a thermistor and a heated filament in the katharometer body. The physically small bead thermistor body 10 is mounted between the two relatively thick terminal rods and 44b, usually of diameter about 1.25 mm (0.05 in), by its two relatively thin terminal wires 50 to about 0.025 mm (0.001 in) diameter which are soldered to the rods. The heat generated in the thermistor by the current has therefore a relatively high resistance leakage path through the wires 50, as compared to the leakage path to the gas passing through the katharometer. Referring to equation (1) it will be seen that the value of $K_L$ is therefore small compared to $K_m$ and $K_i$, while since $K_m$ is much greater than $K_L$ and smaller than $K_i$ for the thermistor the resilient variation in total thermal conductivity is large, with corresponding large variation in the total voltage. The heated filament has no such small heat flow throttling wires but is soldered directly to the heavy terminal rods 44a and 44b, from which the heat generated is transferred easily to the exterior. Consequently the leakage value $K_L$ is high and in practice will be many times the value of $K_m$. The filament is usually of metal and consequently $K_i$ is also very high with the result that most of the heat produced tends to be drained to the exterior through the terminal rods without being removed by the circulating gas. The changes in $K_m$ from changes in the gas cause only small variations in the total thermal conductivity resulting in only small variations in the output voltage. This can only be compensated by increasing the gain of the amplifier, and the variation obtained may be below the input offset voltage required for satisfactory operation of the amplifier to give the sensitivity required.

Figure 5:
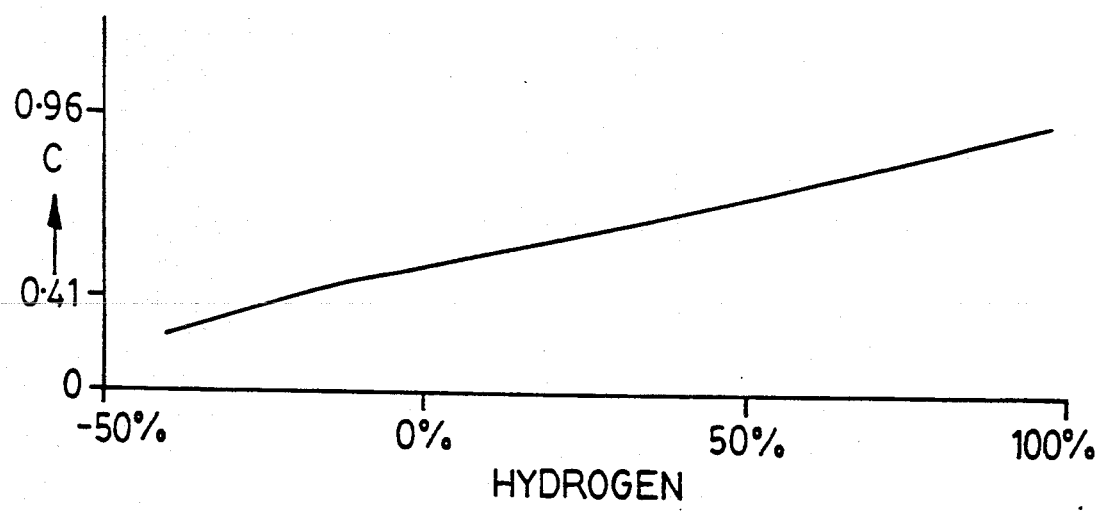
FIG. 5 is a graph showing the response of a circuit of the invention to change of hydrogen content of a test gas.

Since the value of $T_t$ (thermistor temperature) in equation (1) is to be constant the value of its resistance is also corresponding constant, and in order to obtain the greatest output voltage $V_O$ the thermistor resistance should therefore be as high as possible. FIG. 5 shows a series of curves at different ambient temperatures for a value B against the resistance values $R_t$ of the thermistor, where B is given by the following expression derived from equation (1)

$$B = \sqrt{R_t(R_t - T_6)}$$

The thermistor is chosen with the ambient temperature at 60° C. to give maximum value of B at this temperature, it being accepted that the value at the other lower ambient temperatures will be higher.

In this specific example the value of $R_t$ at 60° C. is 960 ohms with a value of B=231; at the lower ambient temperature of 15° C. the value of B is 373.8 and these are the maximum and minimum values of this portion of equation (1); for a given value of $R_t$, which can be obtained with the method and apparatus of the invention, this becomes a constant.

It follows that the final expression $$\sqrt{K_L + \frac{K_i \cdot K_m}{K_i + K_m}}$$

in equation (1), which sets out the total thermal conductivity as seen by the circuit, becomes the only variable and with $K_L$ held to a neglible value by the use of a thermistor the resultant plot of the value of this expression against hydrogen content becomes highly linear, as shown by the graph in FIG. 5, in which the ordinate represents specific numerical values of this final expression. The curve is taken below zero to be able to represent the values obtained with gases other than hydrogen, e.g. argon as used for calibration purposes will give about the same value as −13% $H_2$. At low hydrogen concentrations the value of $K_L$ is about the same order of magnitude as $K_m$ and the slope is greater; in the middle range the graph is virtually linear, while at high values the value of $K_m$ is of the same order of magnitude as $K_i$ which is constant and therefore the linearity is maintained. It will be noted moreover that the graph maintains a substantial positive slope over its entire range up to 100% hydrogen, so that there is no limitation from this aspect on the measurement of high hydrogen concentrations.

The sensitivity of the circuit is given by the slope of the graph in FIG. 5 and it can be shown that for this particular apparatus the variation of $V_O$ to give the required 1% precision in measurement is about 227 microvolts; such a value is within the capabilities of many low cost operational amplifiers. Such low cost amplifiers are also able to meet the modest power requirements required by a katharometer utilizing a thermistor of 30 volts total and about 10 mA output current.

It will be seen therefore that the thermistor utilising katharometers of the invention, and others to be described below, have the desirable characteristics that they are stable and easy to operate and calibrate, provide the desired 1% precision of operation, can measure up to 100% hydrogen content of the test gas without the need to switch ranges, are operable in the desired ambient temperature range of 10° C. to 60° C., and can operate with a requirement for less than 100 milliwatts of electric power than can readily be supplied by batteries in a portable apparatus.

Figure 6:
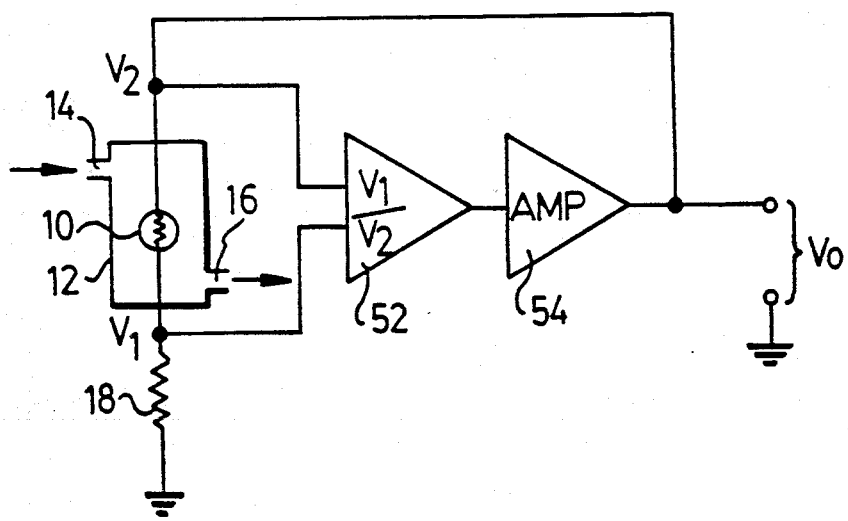
FIG. 6 is a schematic circuit diagram of a second embodiment.
Figure 4:
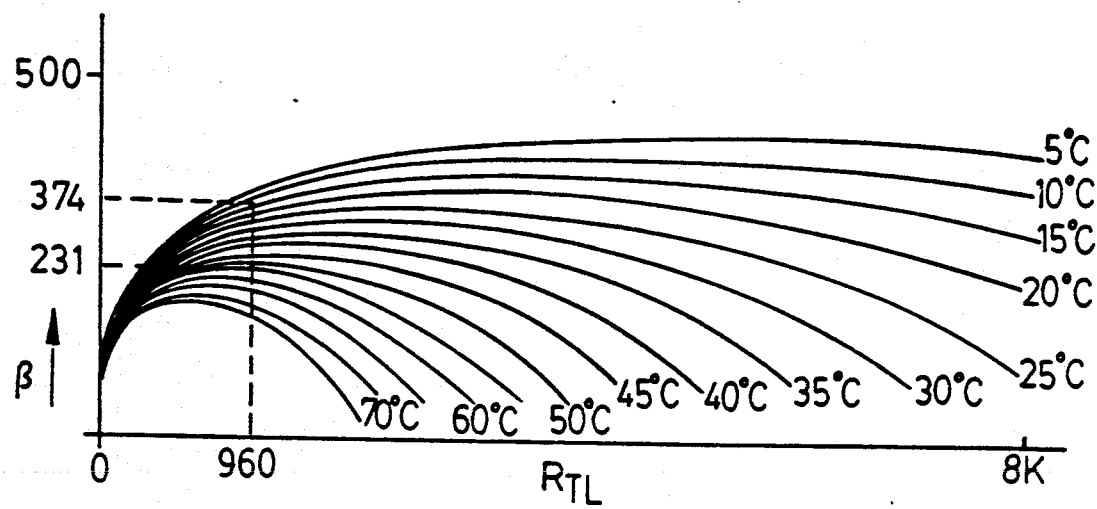
FIG. 4 is a graph of a factor B for a thermistor at different ambient temperatures.

In the circuit of FIG. 6 the same or a similar element is given the same reference number, wherever that is possible. The thermistor element 10 is connected in series with a resistor 18, and is connected across the input of a divider element 52 whose inputs are the potentials, $V_1$ and $V_2$ at the terminals of the thermistor element, and whose output is $V_2/V_1$, this output being fed to an operational amplifier 54. The value of resistor 18 is set to give a desired value (e.g. 2) to the ratio at the predetermined operating temperature and resistance of the element, and the power output of amplifier 54 is sufficient to maintain the ratio stable at that value. As the thermistor 10 cools and its resistance decreases the value of the ratio decreases, whereupon the ouput of amplifier 54 increases to heat the element and restore the resistance to its original equilibrium value. The valve of $V_O$ is measured at the output of the amplifier 54.

Figure 7:
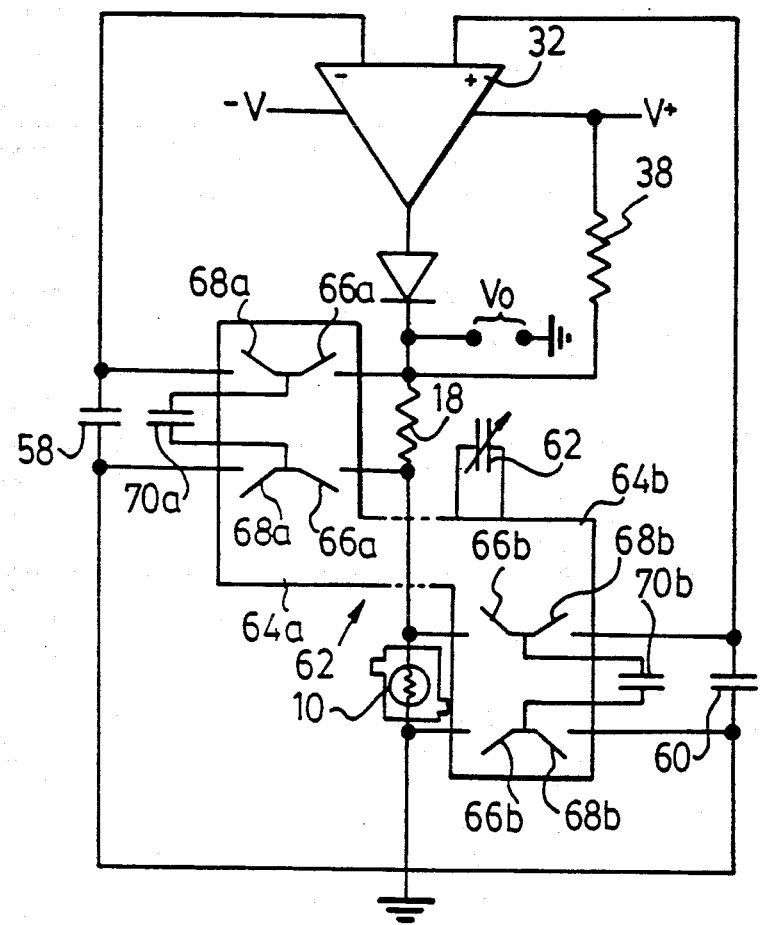
FIG. 7 is a schematic circuit diagram of a third embodiment.

A third embodiment is illustrated by FIG. 7 in which the accuracy and sensitivety of the circuit is improved by eliminating any ambient temperatures effect on the amplifier and the reference resistor 18 of the two previously described circuits, permitting the use of a resistor with a temperature coefficient that is reasonably low (e.g. 50 ppm/°C.) instead of requiring it to be zero, or accepting the otherwise resultant lower sensivity. The amplifier 32 supplies operating current to the thermistor 10 and the reference resistor 18 in series so that they both receive the same current and the voltages across them are therefore equal to their respective resistances; the curcuit is then arranged to control the value $R_{Th}$ of the thermistor to make it equal to the value of resistor 18 at equilibrium, when the voltages are the same, or to bring them to some convenient predetermined ratio. The series connection of the resistor and thermistor makes the comparison of their voltages difficult, since they cannot be directly referenced to a common reference point such as the ground point 56. This difficulty is overcome in the circuits of this aspect of the invention by transferring the voltage value across resistor 18 to a holding capacitor 58, and transferring the voltage value across the thermistor 10 to a holding capacitor 60. The two holding capacitors are connected between the same ground reference point 56 and the respective imputs to the amplifier 32, which can therefore more accurately produce an output such that the two voltages are equal, or are equal to the predetermined ratio. Such a circuit can control the ratio of the values of the voltages with a high degree of precision (e.g. about 2 ppm). Precision capacitors are not required and the operation of the amplifier is independent of ambient temperature. The sensitivity is determined primarily by the input sensitivity of the amplifier, and it is found that the overall precision is better and more stable than an equivalent bridge circuit. The ratio between the two resistances R and $R_{Th}$ must be kept small, but this is not a disadvantage since the value 1 is quite satisfactory, and it is relatively easy to select a resistance sufficiently close in value to the operating range of a thermistor.

In this circuit the voltage transfers are produced by a commercially available dual switching module 62 providing two separate switch blocks 64a and 64b, each including a respective pair of "in" switches 66a and 66b and a pair of "out" switches 68a and 68b. The block 64a controls the voltage transfer from resistor 18 to capacitor 58 via a transfer capacitor 70a, while the block 64b controls the transfer from thermistor 10 to the capacitor 60. When each two "in" switches are closed the respective "out" switches are open, and vice versa, the switches being operated to break before make in both directions under the control of an internal oscillator that synchronises the opening and closing sequences. A suitable range of operating frequency for the switch blocks is from 100 Hz to 1 KHz, the frequency being controlled by an externally adjustable capacitor 72.

Each switch block operates as a differential voltage translator, although theoretically in the circuit as illustrated the block 64b transferring from the thermistor 10 is not essential, since it is already connected to the reference point 56. It is needed in practice so that there is a capacitor at each input to the amplifier; the bias current at each input produces equal voltage variation in both capacitors and a smoother output is obtained. Each transfer capacitor is first connected across its respective resistive element and will charge or discharge until its voltage is equal to that across the element; it is then disconnected and connected to its respective holding capacitor, to which it charges or discharges until their voltages are equal. The switching sequence is repeated and eventually the voltages across each set of resistive element, transfer capacitor and holding capacitor will be equal with the required high degree of accuracy.

We claim:

1. A method for the measurement of gas thermal conductivity employing a katharometer comprising a katharometer enclosure enclosing a katharometer element having a temperature resistance characteristic, the method including:

passing a test gas whose thermal conductivity is to be measured into the katharometer enclosure over a thermistor element to thereby change its temperature from a predetermined value and thereby change its resistance from a corresponding value;

wherein the thermistor is connected in series with a resistor to provide a first potential divider having a respective first junction;

comparing the potential at the first junction with that at the junction of a second potential divider;

employing the result of the comparison corresponding to the change of resistance of the thermistor to change the supply of electrical power to the thermistor to restore its temperature to the predetermined value and its resistance to the corresponding value; and measuring the amount of power supplied to the thermistor with its temperature restored to the predetermined value to determine the test gas thermal conductivity.

2. A method as claimed in claim 1, wherein the potentials at the first and second potential junctions are compared by a differential amplifier, the output of which controls the supply of electrical power to the thermistor.

3. A method as claimed in claim 2, wherein the voltage at the differential amplifier output is measured to determine the gas thermal conductivity.

4. A method as claimed in claim 1, wherein the gas whose conductivity is to be measured is removed from a molten metal by entrainment in a carrier gas.

5. A method as claimed in claim 4, wherein the gas whose conductivity is to be measured is hydrogen and the molten metal is aluminium.

6. A method as claimed in claim 1, and employing two measurements spaced in time to determine the proportion of gas dissolved in the molten metal, the method including circulating a carrier gas through the katharometer enclosure and a probe immersed in the molten metal for a first period of time sufficient to entrain the gas to be determined in the carrier gas to form a mixture of gases, and thereafter making a first measurement; and thereafter purging the katharometer with carrier gas to remove the gas mixture and making a second measurement within a short period of time after the first measurement.

7. A method as claimed in claim 1, wherein a resistor is connected in series with the thermistor to a reference point in the circuit;

the resistor and the thermistor are supplied with current from the same source to establish voltages across them corresponding to their resistances, one of which voltages is measureable from said reference point;

the voltage across at least the other one of the resistor and thermistor not connected directly to the reference point is transferred to another circuit element connected to the reference point; and the voltages having the reference point in common are compared and the current supplied to the resistor and the thermistor is controlled in response to the comparision to maintain their resistances in a predetermined ratio.

8. A method as claimed in claim 7, wherein the voltage across either the resistor or the thermistor is transferred by first transferring it to a transfer capacitor, and thereafter transferring it from the transfer capacitor to a holding capacitor connected to the reference point.

9. A method as claimed in claim 7, wherein the respective voltages across the resistor and the thermistor are transferred by first transferring them to respective transfer capacitors, and thereafter transferring them to respective holding capacitors both connected to the reference point.

10. A method as claimed in claim 9, wherein the current supplied to the resistor and the thermistor in series is controlled by a differential amplifier having the voltages across the two holding capacitors as inputs.

11. Apparatus for the measurement of gas thermal conductivity comprising:

a katharometer body providing an enclosure in its interior having an inlet thereto and an outlet therefrom;

a thermistor element having a temperature/resistance characteristic mounted within the enclosure;

means for supplying electric power to the thermistor to heat it;

means for supplying a gas whose conductivity is to be measured to the interior of the enclosure to thereby change the temperature of the thermistor from a predetermined value and thereby change its resistance from a corresponding value;

control means responsive to the change of resistance of the thermistor to change the amount of electrick power supplied to the element to maintain its temperature at the predetermined value and its resistance at the corresponding value;

the control means comprising a resistance connected in series with the thermistor to constitute a first potential divider having a first junction, a second potential divider having a second junction, and a differential amplifier having two inputs supplied from the respective junctions, the output of the amplifier being connected to the thermistor to control the amount of the electric power supplied to the element; and means for measuring the amount of power required to maintain the thermistor at its predetermined temperature to provide a measurement representative of the thermal conductivity of the gas.

12. Apparatus as claimed in claim 11, wherein the voltage at the amplifier output is measured and is representative of the thermal conductivity of the gas.

13. Apparatus as claimed in claim 11, wherein the thermistor has electrical leads and the leads are mounted on respective isothermal heat sinks to stabilize the leakage thermal resistance thereof.

14. Apparatus as claimed in claim 11, wherein the control means comprises a resistance connected in series with the thermistor;
means for supplying electrical power to the thermistor and the resistance in series to produce voltages across each of them corresponding to their respective resistances;
means for transferring at least one of the voltages thus produced as a first transfer voltage to a common reference point of the circuit with the other voltage; and
means for comparing the two voltages having the common reference point and controlling the supply of electrical power to the thermistor and resistance in series in accordance with the comparison of the two voltages.

15. Apparatus as claimed in claim 14, wherein the control means also includes means for transferring the other oft the two voltage thus produced as a second transfer voltage to the common reference point; and
the said comparing means compares the first and second transfer voltage and controls the supply of electrical power in accordance with the comparison.

16. Apparatus as claimed in claim 14, wherein the transferring means for the resistance or the thermistor comprises a transfer capacitor, a holding capacitor connected to the common reference point, and switch means periodically connecting the transfer capacitor in parallel with the resistance or the thermistor to be charged or discharged thereby, and thereafter connecting the transfer capacitor in parallel with the holding capacitor for the latter to be charged or discharged thereby.

17. Apparatus as claimed in claim 14, wherein the transferring means comprises for each of the resistance and the thermistor a respective transfer capacitor, a respective holding capacitor both connected to the common reference point, and switch means periodically connecting each transfer capacitor in parallel respectively with its resistance and its thermistor to be charge or discharged thereby, and thereafter connecting each transfer capacitor in parallel with it respective holding capacitor for the letter to be charged or discharged thereby.

18. Apparatus as claimed in claim 17, wherein the said comparing means is a differential amplifier having the voltages across the two holding capacitors as inputs.

19. A method for the measurement of gas thermal conductivity employing a katharometer comprising a katharometer enclosure enclosing a katharometer element having a temperature resistance characteristic, the method including:
passing a test gas thermal conductivity is to be measured into the katharometer enclosure over the element to thereby change its temperature from a predetermined value and thereby change its resistance from a corresponding value;
employing the change of resistance of the element to change the supply of electrical power by a power supply circuit to the element to restore its temperature to the predetermined value and its resistance to the corresponding value; and
measuring the amount of power supplied to the element with its temperature restored to the predetermined value to determine the test gas thermal conductivity;
wherein a resistor is connected in series with the element to a reference point in the circuit;
the resistor and the element are supplied with current from the same source to establish voltages across them corresponding to their respective resistances, one of which voltages is measurable from said reference point;
the voltage across at least the other one of the resistor and element not connected directly to the reference point is transferred to another circuit element connected to the reference point; and
the voltages having the reference point in common are compared and the current supplied to the resistor and the element by the circuit is controlled in response to the comparison.

20. A method as claimed in claim 19, wherein the voltage across either the resistor of the element is transferred by first transferring it to a transfer capacitor, and thereafter transferring it from the transfer capacitor to a holding capacitor connected to the reference point.

21. A method as claimed in claim 20, wherein the current supplied to the resistor and the element in series is controlled by a differential amplifier having the voltages across the two holding capacitors as inputs.

22. A method as claimed in claim 19, wherein the respective voltages across the resistor and the element are transferred by first transferring them to respective transfer capacitors, and thereafter transferring them to respective holding capacitors both connected to the reference point.

23. A method as claimed in claim 19, wherein the gas whose conductivity is to be measured is removed from a molten metal by entrainment in a carrier gas.

24. A method as claimed in 23, wherein the gas whose conductivity is to be measured is hydrogen and the molten metal is aluminium.

25. A method as claimed in claim 19, and employing two measurements spaced in time to determine the proportion of gas dissolved in the molten metal, the method including circulating a carrier gas through the katharometer enclosure and a probe immersed in the molten metal for a first period of time sufficient to entrain the gas to be determined in the carrier gas to form a mixture of gases, and thereafter making a first measurement;
and thereafter purging the katharometer with carrier gas to remove the gas mixture and making a second measurement within a short period of time after the first measurment.

26. A method as claimed in claim 19, wherein the katharometer element is a thermistor.

27. Apparatus for the measurement of gas thermal conductivity comprising: a katharometer body providing an enclosure in its interior having an inlet thereto and an outlet therefrom;
a katharometer element having a temperature/resistance characteristic mounted within the enclosure;
means for supplying electric power to the element to heat it;
means for supplying a gas whose conductivity is to be measured to the interior of the enclosure to thereby change the temperature of the element from a predetermined value and thereby change it resistance from a corresponding value;

control means responsive to the change of resistance of the element to change the amount of electric power supplied to the element to maintain its temperature at the predetermined value and its resistance at the corresponding value; and means for measuring the amount of power required to maintain the element at its predetermined temperature to provide a measurement representative of the thermal conductivity of the gas;

wherein the control means comprises a resistance connected in series with the element;

means for supplying electrical power to the element and the resistance in series to produce voltages across each of them corresponding to their respective resistances;

means for transferring at least one of the voltages thus produced as a first transfer voltage to a common reference point of the circuit with the other voltage; and means for comparing the two voltages having the common reference point and controlling the supply of electrical power to the element and resistance in series in accordance with the comparison of the two voltages.

28. Apparatus as claimed in claim 27, wherein the control means also includes means for transferring the other of the two voltage thus produced as a second transfer voltage to the common reference point; and the said comparing means compares the first and second transfer voltage and controls the supply of electrical power in accordance with the comparison.

29. Apparatus as claimed in claim 27, wherein the transferring means for the resistance or the element comprises a transfer capacitor, a holding capacitor connected to the common reference point, and switch means periodically connecting the transfer capacitor in parallel with the resistance or the element to be charged or discharged thereby, and thereafter connecting the transfer capacitor in parallel with the holding capacitor for the latter to be charged or discharged thereby.

30. Apparatus as claimed in claim 27, wherein the transferring means comprises for each of the resistance and the element a respective transfer capacitor, a respective holding capacitor both connected to the common reference point, and switch means periodically connecting each transfer capacitor in parallel respectively with its resistance and its element to be charged or discharged thereby, and thereafter connecting each transfer capacitor in parrallel with its respective holding capacitor for the latter to be charged or discharged thereby.

31. Apparatus as claimed in claim 30, wherein said comparing means if a differential amplifier having the voltages across the two holding capacitors as inputs.

32. Apparatus as claimed in claim 27, wherein the thermistor has electrical leads and the leads are mounted on respective isothermal heat sinks to stabilize the leakage thermal resistance thereof.

33. Apparatus as claimed in claim 27, wherein the katharometer element is a thermistor.

34. A method for the measurement of gas thermal conductivity employing a katharometer comprising a katharometer enclosure enclosing a katharometer element having a temperature resistance characteristic, the method including:

passing a test gas whose thermal conductivity is to be measured into the katharometer enclosure over a thermistor element to thereby change its temperature from a predetermined value and thereby change its resistance from a corresponding value;

employing the change of resistance of the thermistor to change the supply of electrical power to the thermistor to restore its temperature to the predetermined value and its resistance to the corresponding value; and measuring the amount of power supplied to the thermistor with its temperature restored to the predetermined value to determine the test gas thermal conductivity;

the method employing two measurements spaces in times to determine the proportion of gas dissolved in the molten metal, the method including circulating a carrier gas through the katharometer enclosure and a probe immersed in the molten metal for a first period of time sufficient to entrain the gas to be determine in the carrier gas to form a mixture of gases, and thereafter making a first measurement;

and thereafter purging the katharometer with carrier gas to remove the gas mixture and making a second measurement within a short period of time after the first measurement.

* * * * *